US012151009B2

(12) United States Patent
He et al.

(10) Patent No.: US 12,151,009 B2
(45) Date of Patent: Nov. 26, 2024

(54) ENHANCED EFFICIENCY OF SUNSCREEN COMPOSITIONS

(71) Applicants: Beiersdorf AG, Hamburg (DE); Akzo Nobel Chemicals International B.V, Arnhem (NL)

(72) Inventors: Qiwei He, Belle Mead, NJ (US); Michael Timothy Philbin, Hopewell, NJ (US); Gary Theodore Martino, Monmouth Junction, NJ (US); Thomas A. Meyer, Germantown, TN (US); Donathan G. Beasley, Memphis, TN (US); John H. Wagner, Memphis, TN (US)

(73) Assignees: Beiersdorf AG, Hamburg (DE); Akzo Nobel Chemicals International B.V, Arnhem (NL)

( * ) Notice: Subject to any disclaimer, the term of this patent is extended or adjusted under 35 U.S.C. 154(b) by 3 days.

(21) Appl. No.: 16/035,762

(22) Filed: Jul. 16, 2018

(65) Prior Publication Data
US 2018/0318193 A1    Nov. 8, 2018

Related U.S. Application Data

(63) Continuation of application No. 14/163,543, filed on Jan. 24, 2014, now Pat. No. 10,039,700, which is a continuation of application No. 12/628,916, filed on Dec. 1, 2009, now abandoned.

(60) Provisional application No. 61/172,916, filed on Apr. 27, 2009.

(51) Int. Cl.
| | |
|---|---|
| *A61K 8/41* | (2006.01) |
| *A61K 8/04* | (2006.01) |
| *A61K 8/35* | (2006.01) |
| *A61K 8/37* | (2006.01) |
| *A61K 8/42* | (2006.01) |
| *A61K 8/45* | (2006.01) |
| *A61K 8/81* | (2006.01) |
| *A61K 8/86* | (2006.01) |
| *A61Q 17/04* | (2006.01) |

(52) U.S. Cl.
CPC ............ *A61K 8/41* (2013.01); *A61K 8/046* (2013.01); *A61K 8/35* (2013.01); *A61K 8/37* (2013.01); *A61K 8/42* (2013.01); *A61K 8/45* (2013.01); *A61K 8/8147* (2013.01); *A61K 8/86* (2013.01); *A61Q 17/04* (2013.01); *A61K 2800/31* (2013.01)

(58) Field of Classification Search
CPC ... A61K 8/35; A61K 8/37; A61K 8/41; A61K 8/42; A61K 8/45; A61K 8/046; A61K 8/86; A61K 8/8147; A61K 2800/31; A61P 17/16; A61Q 17/04
See application file for complete search history.

(56) References Cited

U.S. PATENT DOCUMENTS

| | | |
|---|---|---|
| 3,206,428 A | 9/1965 | Stanley |
| 3,362,906 A | 1/1968 | Cyba |
| 3,880,992 A | 4/1975 | Smolin et al. |
| 4,132,774 A | 1/1979 | Strobel |
| 4,186,014 A | 1/1980 | Helling et al. |
| 4,683,134 A | 7/1987 | Palinczar |
| 4,731,242 A * | 3/1988 | Palinczar ............... A61K 8/34 |
| | | 424/59 |
| 4,874,604 A | 10/1989 | Sramek |
| 5,410,005 A | 4/1995 | Nemoto et al. |
| 5,645,609 A | 7/1997 | Andrean et al. |
| 5,653,965 A | 8/1997 | Narayanan et al. |
| 5,753,209 A | 5/1998 | Ascione et al. |
| 5,753,215 A | 5/1998 | Mougin et al. |
| 5,776,440 A | 7/1998 | Forestier et al. |
| 5,863,527 A | 1/1999 | Hutchins et al. |
| 5,916,548 A | 6/1999 | Hutchins et al. |
| 5,968,494 A | 10/1999 | Kukkala et al. |
| 5,985,294 A | 11/1999 | Peffly |
| 6,139,827 A | 10/2000 | Cohen et al. |
| 6,162,450 A | 12/2000 | Ptchelintsev et al. |
| 6,231,837 B1 | 5/2001 | Stroud et al. |
| 6,261,541 B1 | 7/2001 | Karpov et al. |
| 6,284,227 B1 | 9/2001 | Stewart |
| 6,372,200 B2 | 4/2002 | Josso et al. |
| 6,410,005 B1 | 6/2002 | Galleguillos et al. |
| 6,482,397 B1 | 11/2002 | Scott et al. |
| 6,488,916 B1 | 12/2002 | Fowler |
| 7,226,585 B2 | 6/2007 | Browning |
| 7,235,230 B2 | 6/2007 | Legrow et al. |
| 7,329,699 B2 | 2/2008 | Liew et al. |

(Continued)

FOREIGN PATENT DOCUMENTS

| | | |
|---|---|---|
| DE | 3518847 A1 | 12/1985 |
| DE | 102005059742 A1 | 6/2007 |

(Continued)

OTHER PUBLICATIONS

Acrylates and Acrylic Acids: https://cameochemicals.noaa.gov/react/71. Retrieved on Jun. 26, 2019.*
"Dimethyl Stearamine: retrieved from internet http:/www.thegoodscentscompany.com/data/rw1303771.html. Retrieved on Jan. 9, 2017".
English Translation for Publication No. DE102005059742A1.
European Search Report for EP Application No. 09163327.1, Completion Date Nov. 24, 2009.
Office Action for Japanese Application No. JP2012507463 dated Jun. 3, 2014.

(Continued)

*Primary Examiner* — Hong Yu
(74) *Attorney, Agent, or Firm* — Abel Schillinger, LLP

(57) ABSTRACT

Compositions comprising UV blocking agents, a film forming polymer containing acid groups and a neutralizing agent; compositions and methods for increasing the SPF of a composition by neutralizing at least a portion of the acid groups of the film forming agent with the neutralizing agent.

17 Claims, No Drawings

(56) References Cited

U.S. PATENT DOCUMENTS

| | | |
|---|---|---|
| 7,423,394 B2 | 9/2008 | Collins |
| 8,440,172 B2 | 5/2013 | Johncock et al. |
| 10,039,700 B2 * | 8/2018 | He .................... A61K 8/046 |
| 2002/0028223 A1 | 3/2002 | Vatter et al. |
| 2002/0155962 A1 | 10/2002 | Cincotta et al. |
| 2003/0077240 A1 | 4/2003 | Legrow et al. |
| 2003/0191154 A1 | 10/2003 | Kalafsky et al. |
| 2004/0157042 A1 | 8/2004 | Ackerman et al. |
| 2004/0231070 A1 | 11/2004 | Morrissey et al. |
| 2004/0258648 A1 | 12/2004 | Creamer et al. |
| 2005/0153135 A1 | 7/2005 | Popplewell et al. |
| 2005/0226900 A1 | 10/2005 | Winton et al. |
| 2006/0112503 A1 | 6/2006 | Hatano et al. |
| 2006/0117637 A1 | 6/2006 | Jeckle |
| 2006/0134045 A1 | 6/2006 | Cao et al. |
| 2006/0233727 A9 | 10/2006 | Huggins et al. |
| 2007/0025943 A1 | 2/2007 | Patel |
| 2007/0059262 A1 | 3/2007 | Taniguchi |
| 2007/0059263 A1 | 3/2007 | Taniguchi et al. |
| 2007/0060650 A1 | 3/2007 | Taniguchi et al. |
| 2007/0060666 A1 | 3/2007 | Taniguchi et al. |
| 2007/0207174 A1 | 9/2007 | Pluyter et al. |
| 2007/0269396 A1 | 11/2007 | Philbin et al. |
| 2008/0014155 A1 | 1/2008 | Marrs |
| 2008/0019927 A1 | 1/2008 | Zhang et al. |
| 2008/0020004 A1 | 1/2008 | Birkel et al. |
| 2008/0070993 A1 | 3/2008 | Borbely |
| 2008/0081024 A1 | 4/2008 | Beasley et al. |
| 2008/0247975 A1 | 10/2008 | Dueva-Koganov et al. |
| 2008/0312395 A1 | 12/2008 | Muller et al. |
| 2009/0035234 A1 | 2/2009 | Cunningham et al. |
| 2009/0257960 A1 * | 10/2009 | Kim .................... A61K 8/41 424/47 |
| 2010/0272657 A1 | 10/2010 | He et al. |
| 2010/0272658 A1 | 10/2010 | He et al. |
| 2011/0189113 A1 | 8/2011 | Ross et al. |
| 2012/0195839 A1 | 8/2012 | He et al. |
| 2014/0219927 A1 | 8/2014 | Belluscio et al. |
| 2014/0255478 A1 | 9/2014 | Martino |
| 2015/0139930 A1 | 5/2015 | Chandran et al. |
| 2016/0015621 A1 | 1/2016 | Martino et al. |

FOREIGN PATENT DOCUMENTS

| | | |
|---|---|---|
| DE | 102006007547 A1 * | 8/2007 |
| EP | 1213010 A2 | 6/2002 |
| JP | 862265215 A | 11/1987 |
| JP | H01160914 A | 6/1989 |
| WO | 9520641 A1 | 8/1995 |
| WO | 0015190 A1 | 3/2000 |
| WO | 2004071479 A1 | 8/2004 |
| WO | 2007068699 A1 | 6/2007 |
| WO | 2007128840 A2 | 11/2007 |
| WO | 2007135197 A2 | 11/2007 |
| WO | WO 2007/128776 A1 * | 11/2007 |
| WO | 2009023662 A2 | 2/2009 |

OTHER PUBLICATIONS

"Office Action for U.S. Appl. No. 14/623,983 mailed Sep. 8, 2017".
PCT Search Report for International Application No. PCT/US2010/032354 mailed Feb. 24, 2012.
PCT Search Report for International Application No. PCT/US2010/032356 mailed Feb. 24, 2012.
ROC (Taiwan) Search Report for Patent Application No. 099 11371.
ROC (Taiwan) Search Report (Translation) for Patent Application No. 099113369 dated Sep. 25, 2012.
Women Surfers Share Sun-protection Secrets, Retrieved from the Internet: http://www.latimes.com/la-ig-beauty20-2008jul20-story.html [Retrieved on Nov. 8, 2016].

* cited by examiner

ENHANCED EFFICIENCY OF SUNSCREEN COMPOSITIONS

This application claims priority to U.S. Application Ser. No. 61/172,916, filed Apr. 27, 2009, the contents of which are hereby incorporated by reference into this specification in its entirety. This application is also related to U.S. application Ser. No. 12/628,924, filed Dec. 1, 2009, the contents of which are hereby incorporated by reference into this specification in its entirety.

FIELD OF INVENTION

This invention relates generally to compositions applied topically to surfaces, for example skin and hair, for protection against ultraviolet radiation. The invention also relates to compositions and methods to improve skin feel and sunscreening capacity of such compositions.

BACKGROUND OF THE INVENTION

Sunscreen compositions are typically categorized as either aqueous or non-aqueous, i.e, anhydrous, compositions. Aqueous sunscreen compositions are typically creams formed as emulsions containing the active UV absorbing compounds and additional ingredients such as waterproofing agents, fragrances, emollients and other skin care ingredients. Non-aqueous sunscreen compositions are those that are typically solvent based compositions that can be formed as gels for topical application or sprayed on, for example from an alcohol based solution of the ingredients.

Sprayable sunscreen compositions have become popular in recent years as a means for transporting and applying sunscreen. Film forming polymers are known to be added to non-aqueous sunscreen compositions to provide water resistance to these compositions after application to a surface such as skin or hair. However, it has been determined that the addition of the film forming polymers beyond a certain amount can have a deleterious effect on the feel of the composition on the skin, in particular providing a caking feeling. Neutralizing agents have been used in connection with film forming agents contained in aqueous sunscreen emulsion formulations. See, e.g., WO 2004/071749 (Connetics Australia Pty. Ltd.) discussing limiting the amount of neutralizing agent added to aqueous formulations to preserve film forming properties.

In an effort to improve the skin feel of topically applied anhydrous sunscreen compositions that employ film forming polymers as waterproofing agents, the inventors have discovered that certain neutralizing agents provide not only the desired improved skin feel, but also provide an unexpected substantial boost in SPF values. Thus, compositions and methods employing such neutralizing agents to provide for improved sunscreen protection would be useful. These and other objectives are provided by the invention described herein.

All patent and non-patent references cited herein are hereby incorporated in their entirety into this specification by reference thereto. Identification or discussion of any reference in this section or any part of this specification shall not be construed as an admission that such reference is available as prior art to the present application.

SUMMARY OF THE INVENTION

The invention provides an anhydrous composition comprising at least one UV absorbing active ingredient and at least one film forming polymer containing a plurality of acid groups, wherein the polymer is present in an amount greater than about 1% by weight of the composition and wherein at least a portion of the acid groups have been neutralized with a neutralizing agent.

The invention further provides a method for increasing the SPF for an anhydrous composition comprising at least one sunscreen active agent and at least one film forming polymer, wherein the film forming polymer comprises a plurality of acid groups, the method comprising adding a cosmetically acceptable neutralizing agent to the composition resulting in the formation of a composition containing at least one sunscreen active agent and a film forming agent wherein at least a portion of the acid groups are neutralized by a cosmetically acceptable neutralizing agent, and wherein the film forming agent is present in an amount greater than 1% by weight of the final composition.

The invention also provides a method for increasing the SPF of an anhydrous composition comprising at least one sunscreen active agent, which comprises adding to the composition a film forming polymer containing a plurality of acid groups and a cosmetically acceptable neutralizing agent, resulting in the formation of a composition containing said at least one sunscreen active agent and a film forming agent wherein at least a portion of the acid groups are neutralized by said neutralizing agent, wherein the film forming polymer is present in an amount greater than 1% by weight of the final composition.

The invention further provides a method for increasing the SPF of a composition comprising at least one sunscreen active agent, which comprises contacting a film forming polymer containing a plurality of acid groups with a cosmetically acceptable neutralizing agent to form a neutralized film forming agent wherein at least a portion of the acid groups are neutralized by said neutralizing agent, and adding to the composition comprising at least one sunscreen active agent the neutralized film forming agent, resulting in the formation of a composition containing said at least one sunscreen active agent and said neutralized film forming agent, wherein the film forming agent is present in an amount greater than 1% by weight of the final composition.

The invention further provides a method for reducing the deleterious effects of UV radiation that contacts a surface which comprises applying to the surface the compositions of the invention.

The invention also provides a method for preventing or reducing the occurrence of erythema on a subject due to exposure to UV radiation which comprises applying the composition of the invention to the subject prior to exposure to UV radiation.

The invention also provides a method for preventing or reducing the occurrence of phototoxic or photoallergic reactions in a subject due to exposure to UV radiation which comprises applying the composition of the invention to the subject prior to exposure to UV radiation.

DETAILED DESCRIPTION OF THE INVENTION

The invention provides an anhydrous composition comprising at least one UV absorbing active ingredient and at least one film forming polymer containing a plurality of acid groups, wherein the polymer is present in an amount greater than 1% by weight of the composition and wherein at least a portion of the acid groups have been neutralized with a cosmetically acceptable neutralizing agent.

While many cosmetically acceptable neutralizing agents are available and will function in this application, surprisingly amine-based neutralizing agents provide a synergistic boost in SPF levels. The amine-based neutralizing agents of the invention can comprise a primary, secondary, or tertiary amine containing one or more hydrocarbon chains having at least 3 carbon atoms. Thus, in one example embodiment, the neutralizing agent of the invention comprises one or more amines of the structure I:

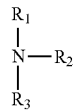

I wherein $R_1$ is H or a $C_3$-$C_{36}$, in another embodiment, $C_3$-$C_{24}$, and in still another embodiment, $C_6$-$C_{18}$ straight chain, branched or cyclic alkyl, alkenyl, alkynyl, aryl, aralkyl, aralkenyl, or aralkynyl group, $R_2$, $R_3$, are independently selected from H, $CH_3$, or a $C_2$ to about $C_{36}$ straight chain, branched or cyclic alkyl, alkenyl, alkynyl, aryl, aralkyl, aralkenyl, or aralkynyl group, provided that $R_1$, $R_2$, and $R_3$ are not all H. The alkyl, alkenyl, alkynyl, aryl, aralkyl, aralkenyl, and aralkynyl group may optionally comprise one or more heteroatoms including S, N, O, and Si. In one embodiment of this invention, the one or more side chains ($R_1$, $R_2$ and $R_3$) will contain six or more carbon atoms (total of all chains). In another embodiment one chain will contain six or more carbon atoms.

In certain embodiments the amine-based neutralizing agents of the invention will comprise one or more of the structures Ia-Id:

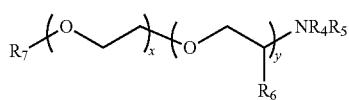

Ia

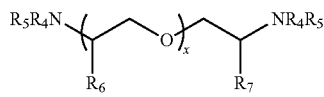

Ib

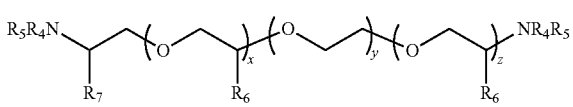

Ic

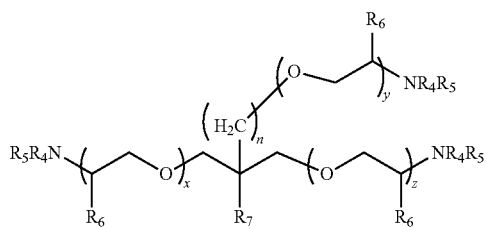

Id wherein $R_4$, $R_5$, $R_6$, and $R_7$, are independently selected from H, $CH_3$, or a $C_2$ to about $C_{36}$ straight chain, branched or cyclic alkyl, alkenyl, alkynyl, aryl, aralkyl, aralkenyl, or aralkynyl group. The alkyl, alkenyl, alkynyl, aryl, aralkyl, aralkenyl, and aralkynyl group may optionally comprise one or more heteroatoms including S, N, O, and Si.

Compounds of this type include the products known as JEFFAMINE® polyetheramines (available from Huntsman Chemical Co, The Woodlands, TX), including those having the following structures Ie through Ih:

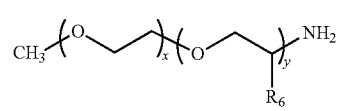

Ie wherein $R_6$ is H or $CH_3$;

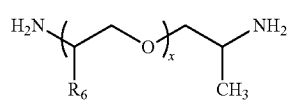

If

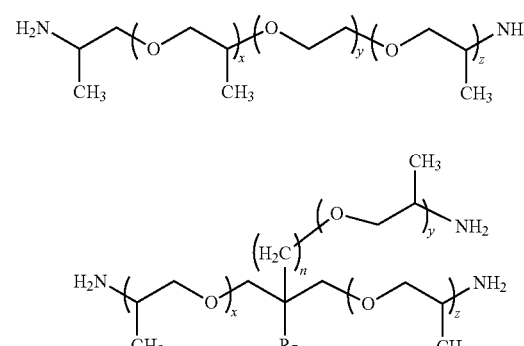

Ig and

Ih

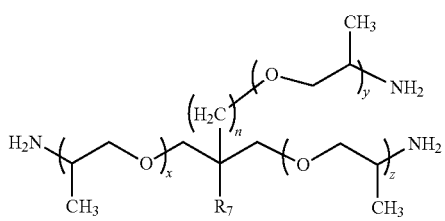

wherein $R_7$ is H or $C_2H_5$.

In another embodiment, the amine-based neutralizing agent is selected from one or more compounds of structures II and/or III:

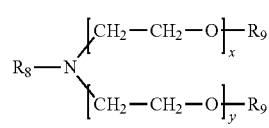

II

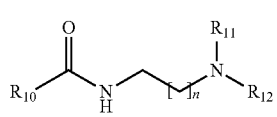

III wherein $R_8$, $R_9$, $R_{10}$, $R_{11}$, $R_{12}$ are independently H, $CH_3$, or a $C_2$ to about $C_{36}$ straight chain, branched or cyclic alkyl, alkenyl, alkynyl, aryl, aralkyl, aralkenyl, or aralkynyl group. The alkyl, alkenyl, alkynyl, aryl, aralkyl, aralkenyl, and aralkynyl group may optionally comprise one or more heteroatoms including S, N, O, and Si.

In another example embodiment, the neutralizing agent of the invention may also comprise amine groups contained within or pendant from additional molecules, such as a monomer unit within a larger polymer or pendant from a polymer backbone. Thus neutralizing agent may comprise primary or secondary amines as pendant groups or monomer units wherein the amines can be optionally substituted with $C_2$ to a $C_{36}$ straight chain, branched or cyclic alkyl, alkenyl, alkynyl, aryl, aralkyl, aralkenyl, or aralkynyl group. The alkyl, alkenyl, alkynyl, aryl, aralkyl, aralkenyl, and aralkynyl group may optionally comprise one or more of S, N, O, or Si. The polymer backbone contemplated herein may comprise, for example, a silicone polymer or acrylic acid polymer.

In certain example embodiments as shown structurally above, each of n, x, y, and z, are independently from 0 up to 100, up to 90, up to 80, up to 70, up to 60, up to 50, up to 40, up to 30, up to 20, or up to 10. In certain example embodiments of the invention, $R_1$, $R_2$, $R_3$, and $R_4$ will independently comprise moieties having up to 50 carbon atoms. In certain example embodiments, $R_1$-$R_{12}$ will independently comprise moieties having up to 40 carbon atoms. In certain example embodiments, $R_1$-$R_{12}$ will independently comprise moieties having up to 30 carbon atoms. In certain example embodiments, $R_1$-$R_{12}$ will independently comprise moieties having up to 20 carbon atoms. Some non-limiting examples of amine neutralizing agents appropriate for this invention are alkyl amines, alkenyl amines, dialkyl amines, dialkenyl amines, dimethyl alkyl amines (alkyl being stearyl, tallow, cocoyl, soy etc), methyl dialkyl amines (alkyl being stearyl, hexadecyl, tallow) and trialkyl amines, dimethyl alkenyl amines (alkenyl being soy, oleic, linoleic and linolenic), methyl dialkenyl amines and triaklenyl amines and combinations thereof.

In the practice of the invention, the amine neutralizing agent acts to neutralize at least a portion of the acid groups, e.g., carboxylic, sulfonic, phosphoric or similar acid groups, on the film forming polymer. Thus, the film forming polymer can be partially neutralized or fully neutralized by the neutralizing agent. In certain example embodiments between about 5% and about 100% the acid groups on the film forming polymer will be neutralized. In other example embodiments up to about 90%, up to about 80%, up to about 70%, up to about 60%, up to about 50%, up to about 40%, up to about 30%, up to about 25%, up to about 20%, up to about 15%, up to about 10% or up to about 5% of the acid groups on the film forming polymer will be neutralized.

In the practice of the invention, the amount of amine neutralizing agent to be added to obtain the desired percent neutralization of the polymer film forming agent can be determined based on the acidity of the polymer and the neutralization equivalent of the amine neutralizing agent. For example, the following equation can be used to determine the precise amount of neutralizing agent:

$$\text{Amount of Neutralizing Agent (g)} = \frac{W * A * N * E}{100{,}000}$$

W=wt. of polymer film former in grams
A=acidity of polymer film former (meq/g)
N=% of desired neutralization
E=neutralization equivalent of amine (g/eq)

The acidity of particular film forming agents is readily available. For example the acidity of the film forming polymer DERMACRYL® 79 is 2.27 meq/g. The neutralization equivalent (E) for various amine neutralizing agents is also readily available. Examples of some Armeen® and Ethomeen® amine neutralizing agents is shown in Table 1 below.

TABLE 1

| Product Name | INCI Name | Neutralization Equivalent (g/eq) |
|---|---|---|
| Armeen ® M2C | Methyl Dicocamine | 398 |
| Armeen ® DMSVD | Dimethyl Soyamine | 306 |
| Armeen ® DMCD | Dimethyl Cocamine | 240 |
| Ethomeen ® SV12 | PEG-2 Soyamine | 357 |
| Ethomeen ® C12 | PEG-2 Cocamine | 292 |
| Ethomeen ® SV15 | PEG-5 Soyamine | 474 |
| Ethomeen ® C15 | PEG-5 Cocamine | 413 |
| Ethomeen ® SV25 | PEG-15 Soyamine | 935 |
| Ethomeen ® C25A | PEG-15 Cocamine | 848 |

In the practice of the invention, the amine neutralizing agent may be combined with the film forming polymer to provide a partially or fully neutralized polymer to be added later to the remainder of the composition. Alternatively, the amine neutralizing agent may be added with the film forming polymer as part of the composition, accomplishing the partial or complete neutralization in situ.

In one example embodiment of the invention, the film forming polymer comprises at least 5% by weight of an acid-containing monomer. In additional example embodiments, the film forming polymer comprises at least 5% by weight of an carboxylic acid-containing monomer. Non-limiting examples of these monomers are acrylic acid, crotonic acid, methacrylic acid, maleic acid, itaconic acid and combinations and mixtures thereof. Additional film forming polymers, either synthetic or natural can be used with the acid containing polymers described above. Non-limiting examples of these additional film forming polymers are: from National Starch and Chemical Company, AMPHOMER® and AMPHOMER® LV-71 polymers (octylacrylamide/acrylates/butylaminoethyl methacrylate compolymer), AMPHOMER HC® polymer (acrylates/octylacrylamide copolymer) BALANCE® 0/55 and BALANCE CR® polymers (acrylates copolymer), BALANCE® 47 polymer (octylacrylamide/butylaminoethyl methacrylate copolymer), RESYN® 28-2930 polymer (VA/crotonates/vinyl neodecanoate copolymer), RESYN® 28-1310 polymer (VA/Crotonates copolymer), FLEXAN® polymers (sodium polystyrene sulfonate), DynamX polymer (polyurethane-14 (and) AMP-Acrylates copolymer), RESYN XP® polymer (acrylates/octylacrylamide copolymer), STRUCTURE 2001 (acrylates/steareth-20 itaconate copolymer) and STRUCTURE® 3001 (acrylates/ceteth-20 itaconate copolymer); from ISP, OMNIREZ-2000® (PVM/MA half ethyl ester copolymer), GANEX P-904® (butylated PVP), GANEX V-216® (PVP/hexadecene copolymer) GANEX® V-220 (PVP/eicosene copolymer), GANEX® WP-660 (tricontanyl PVP), GANTREZ® A425 (butyl ester of PVM/MA copolymer), GANTREZ® AN-119 PVM/MA copolymer, GANTREZ ES 225® (ethyl ester of PVM/MA copolymer), GANTREZ ES425 (butyl ester of PVM/MA copolymer), GAFFIX VC-713® (vinyl caprolactam/PVP/dimethylaminoethyl methacrylate copolymer), GAFQUAT 755® (polyquaternium-11), GAFQUAT HS-100® (polyquaternium-28) AQUAFLEX XL-30® (Polyimide-1), AQUAFLEX SF-40® (PVP/Vinylcaprolactam/DMAPA Acrylates Copolymer), AQUAFLEX FX-64® (Isobutylene/Ethylmaleimide/Hydroxyethylmaleimide Copolymer), ALLIANZ LT-120® (Acrylates/C1-2 Succinates/Hydroxyacrylates Copolymer), STYLEZE CC-10® (PVP/DMAPA Acrylates Copolymer), STYLEZE 2000® (VP/Acrylates/Lauryl Methacrylate Copolymer), STYLEZE W-20® (Polyquaternium-55), Copolymer Series (PVP/Dimethylaminoethylmethacrylate Copolymer), ADVANTAGE S® and ADVANTAGE LCA® (VinylcaprolactamNP/Dimethylaminoethyl Methacrylate Copolymer), ADVANTAGE PLUS (VA/Butyl Maleate/Isobornyl Acrylate Copolymer); from BASF, ULTRAHOLD STRONG (acrylic acid/ethyl acrylate/t-butyl acrylamide), LUVIMER 100P® (t-butyl acrylate/ethyl acrylate/methacrylic acid), LUVIMER 36D (ethyl acrylate/t-butyl acrylate/methacrylic acid), LUVIQUAT HM-552® (polyquaternium-16), LUVIQUAT HOLD® (polyquaternium-16), LUVISKOL K30 (PVP) LUVISKOL K90® (PVP), LUVISKOL VA 64® (PVP/VA copolymer) LUVISKOL VA73W® (PVPNA copolymer), LUVISKOL VA®, LUVISET PUR® (Polyurethane-1), LUVISET® Clear (VP/MethacrylamideNinyl Imidazole Copolymer), LUVIFLEX SOFT® (Acrylates Copolymer), ULTRAHOLD 8® (Acrylates/Acrylamide Copolymer), LUVISKOL® Plus (Polyvinylcaprolactam), LUVIFLEX® Silk (PEG/PPG-25/25 Dimethicone/Acrylates Copolymer); from Amerchol, AMERHOLD® DR-25 (acrylic acid/methacrylic acid/acrylates/methacrylates); from Rohm&Haas, ACLTDYNE 258® (acrylic acid/methacrylic acid/acrylates/methacrylates/hydroxy ester acrylates; from Mitsubishi and distributed by Clariant, DIAFORMER Z-301®, DIAFORMER Z-SM®, and DIAFORMER Z-400® (methacryloyl ethyl betaine/acrylates copolymer), ACUDYNE 180® (Acrylates/Hydroxyesters Acrylates Copolymer), ACUDYNE SCP® (Ethylenecarboxyamide/AMPSA/Methacrylates Copolymer), and the ACCULYN® rheological modifiers; from ONDEO Nalco, FIXOMER A-30® and FIXOMER N-28 ® (INCI names: methacrylic acid/sodium acrylamidomethyl propane sulfonate copolymer); from Noveon, FIXATE G-100® (AMP-Acrylates/Allyl Methacrylate Copolymer), FIXATE PLUS® (Polyacrylates-X), CARBOPOL® Ultrez 10 (Carbomer), CARBOPOL Ultrez 20® (Acrylates/C10-30 Alkyl Acrylates Copolymer), AVALLTRE AC® series (Acrylates Copolymer), AVALURE UR® series (Polyurethane-2, Polyurethane-4, PPG-17/IPDI/DMPA Copolymer); polyethylene glycol; water-soluble acrylics; water-soluble polyesters; polyacrylamides; polyamines; polyquaternary amines; styrene maleic anhydride (SMA) resin; polyethylene amine; and other conventional polymer that is polar solvent soluble or that can be made soluble through neutralization with the appropriate base.

Additional natural film forming polymers are native starch as used herein, also starches derived from a plant obtained by standard breeding techniques including crossbreeding, translocation, inversion, transformation or any other method of gene or chromosome engineering to include variations thereof. In addition, starch derived from a plant grown from artificial mutations and variations of the above generic composition, which may be produced by known standard methods of mutation breeding, are also suitable herein.

One skilled in the art would recognize that the film forming polymer may comprise a blend of two of more polymers. In one example embodiment of the invention, a blend of polymers may be used, wherein at least one of the polymers contains a carboxylic acid monomer and the level of carboxylic acid monomer is no less than 5% of the total polymer (by weight dry basis of the total film forming polymer).

Sunscreen compositions according to the invention are prepared as non-aqueous, volatile solvent-based compositions. The terms "non-aqueous" and "anhydrous" are used interchangeably herein and refer to compositions containing less than about 10% by weight water. Thus, the compositions comprise a single liquid phase that may further comprise dispersed particulates. In certain embodiments the compositions of the invention will contain less than about 5% by weight water or less than 1% by weight water. Example volatile solvents include one or more of alcohols such as methanol, ethanol and isopropanol, volatile hydrocarbons such as isooctane, isododecane, and isohexadecane, aldehydes and volatile silicones also including volatile ketones such as acetone and methyl ethyl ketone. In an embodiment of this invention the volatile solvent is chosen from the group consisting of ethanol, methanol, isopropanol and acetone. The sunscreen compositions of the invention containing alcohol based solvent systems are characterized as non-aqueous solutions. However, it may be desirable to have small amount of water in the composition, for example as a processing aid or co-solvent. In certain example embodiments, the water contents of the compositions will be no greater than about 9% water so as to prevent the active to phase separate or precipitate out of solution. Those of ordinary skill in the art will recognize that different actives have different tolerance for water in solution and will adjust water content accordingly. Additionally, the solvent can include an oil such as mineral or vegetable oil. The oil may be the only solvent or may be used in varying amounts as a co-solvent or as described herein as "emollients".

For purposes of the present invention, a "sunscreen active agent" or "sunscreen active" shall include all of those materials, singly or in combination, that are regarded as acceptable for use as active sunscreening ingredients based on their ability to absorb UV radiation. Such compounds are generally described as being UV-A, UV-B, or UV-A/UV-B active agents. Approval by a regulatory agency is generally required for inclusion of active agents in formulations intended for human use. Those active agents which have been or are currently approved for sunscreen use in the United States include organic and inorganic substances including, without limitation, para aminobenzoic acid, avobenzone, cinoxate, dioxybenzone, homosalate, menthyl anthranilate, octyl salicylate, oxybenzone, padimate O, phenylbenzimidazole sulfonic acid, sulisobenzone, trolamine salicylate, titanium dioxide, zinc oxide, diethanolamine methoxycinnamate, digalloy trioleate, ethyl dihydroxypropyl PABA, glyceryl aminobenzoate, lawsone with dihydroxyacetone, red petrolatum. Examples of additional sunscreen actives that have not yet been approved in the US but are allowed in formulations sold outside of the US include ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. However, as the list of approved sunscreens is currently expanding, those of ordinary skill will recognize that the invention is not limited to sunscreen active agents currently approved for human use but is readily applicable to those that may be allowed in the future.

In one embodiment of the invention the sunscreen active agent comprises a photoprotecting effective amount of particulates of at least one inorganic pigment or nanopigment, non-limiting examples of which include titanium dioxide, zinc oxide, iron oxide, zirconium oxide, cerium oxide, or mixture thereof.

The compositions of this invention can be applied to the skin as a liquid rub on, but are most commonly applied as a spray. However, the compositions are not limited to those compositions applied to the skin primarily as a sunscreen agent. The compositions also incorporate those formulations where the sunscreen active agent is an ingredient in another topically applied composition. Some non-limiting examples are lipstick, make-up, lip-balm, eye-shadow, hair dyes and conditioners, or any application where sun protection may be deemed beneficial.

In certain embodiments of the subject invention, the compositions can be stored in containers under pressure by combination with a propellant. The compositions thus stored can be applied by opening a valve in the container releasing the propellant and the composition, typically in a spray or mist. The propellant used in the composition may be any suitable gas, or combination of gasses, that can be compressed or liquefied within a dispensing spray canister, which expand or volatilize to vapor or gas form upon exposure to ambient temperature and pressure conditions to deliver the composition in an aerosol form. Suitable propellants include hydrocarbons having 1 to 5 carbon atoms, including but not limited to methane, ethane, propane, isopropane, butane, isobutane, butene, pentane, isopentane, neopentane, pentene, hydrofluorocarbons (HFCs), chlorofluorocarbons (CFCs), nitrogen, ethers including dimethyl ether, and any mixtures thereof. Those of ordinary skill in the art recognize that in a closed container such as an aluminum can or glass bottle, propellants such as dimethyl ether condense to the liquid state at ambient temperature. Thus, the composition in the aerosol container is liquid formulation which can contain dissolved propellant, undissolved liquid propellant and gaseous propellant. All of this is under pressure due to the vapor pressure of the propellant. In the practice of this aspect of the subject invention, the propellant can be present in an amount up to about 90 weight percent, preferably from about 2 weight percent to about 50 weight percent, and more preferably about 5 weight percent to about 40 weight percent, more preferably at about 30 weight percent, based on the total weight of the aerosol composition.

The compositions of the present invention may contain a wide range of additional, optional components which are referred to herein as "cosmetic components", but which can also include components generally known as pharmaceutically active agents. The CTFA Cosmetic Ingredient Handbook, Seventh Edition, 1997 and the Eighth Edition, 2000, which is incorporated by reference herein in its entirety, describes a wide variety of cosmetic and pharmaceutical ingredients commonly used in skin care compositions, which are suitable for use in the compositions of the present invention. Examples of these functional classes disclosed in this reference include: absorbents, abrasives, anticaking agents, antifoaming agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, SPF boosters, waterproofing agents, and viscosity increasing agents (aqueous and nonaqueous).

The compositions of the invention may also include materials that also increase the SPF of the final composition by such mechanisms as UV radiation scattering and dispersion. Such materials are referred to herein as "UV-radiation scattering agents" and comprise materials that exhibit UV absorbing activity or exhibit no UV absorbing activity. An example of such UV-radiation scattering agents include polymeric materials, such as the product known as SunSpheres™ (Rohm and Haas; Philadelphia, PA) which are described by their manufacturer as hollow styrene/acrylates copolymer spheres manufactured by emulsion polymerization. The polymer spheres are said to raise SPF values across the UVA and UVB region by dispersing and/or scattering the incident UV radiation throughout the film of sunscreen present on a surface, such as human skin. It is understood that the spheres cause less UV radiation to penetrate into the skin by redirecting the radiation towards the UV-absorbing sunscreen actives in the sunscreen formulation, where the radiation reacts with the sunscreen active molecules and the energy is dissipated as heat. As used herein, the terms "spheres" or "scattering agents" are not limited by chemical makeup or shape, but comprise any agent that produces the effect of lengthening the path of incident UV radiation, increasing the statistical likelihood that the radiation will contact a sunscreen active molecule, i.e., a UV absorbing active agent. These materials may also include UV absorbing materials that also exhibit scattering properties such as ZnO (examples include Z-Cote™ products available from BASF), $TiO_2$ (examples include the Solaveil™ products available from Uniqema (New Castle, DE, USA)), compounds such as methylene bis-benzotriazolyl tetramethylbutylphenol, ("Tinasorb™ M" available from Ciba Specialty Chemicals, Inc. (Basel, Switzerland). UV radiation scattering agents are typically present in the formulation in amounts up to about 25% by weight. Certain example embodiments of the invention may comprise up to about 10% by weight, preferably in ranges of about 0.5% to about 7.0% by weight, in particularly preferred ranges of 3% to about 5% by weight.

As used herein, the terms "sunless-tanning agent" or "self-tanning compositions" refer to compositions which, when applied to human skin, impart thereto an appearance similar to that achieved by exposing the skin to natural or artificial sunlight. Examples of sunless tanning active agents are described in U.S. Pat. Nos. 6,482,397, 6,261,541, and 6,231,837. Such sunless tanning compositions typically comprise, in addition to an artificial tanning effective amount of a self tanning agent, effective amounts of a composition coloring agent and a cosmetically acceptable carrier adapted for topical application to human skin. The self tanning agents can also include those compositions generally accepted in the art for application to human skin, and which, when so applied, react therein with amino acids so as to form pigmented products. Such reactions give the skin a brown appearance similar to the color obtained upon exposing it to sunlight for periods of time sufficient to tan the skin. Suitable self tanning agents include, without limitation, alpha-hydroxy aldehydes and ketones, glyceraldehyde and related alcohol aldehydes, various indoles, imidazoles and derivatives thereof, and various approved pigmentation agents. Presently preferred herein as self tanning agents are the alpha-hydroxy aldehydes and ketones. Most preferably, the self tanning agent is dihydroxyacetone ("DHA"). Other suitable self tanning agents include, without limitation, methyl glyoxal, glycerol aldehyde, erythrulose, alloxan, 2,3-dihydroxysuccindialdehyde, 2,3-dimethoxysuccindialdehyde, 2-amino-3-hydroxy-succindialdehyde and 2-benzylamino-3-hydroxysuccindialdehyde.

An emollient is an oleaginous or oily substance which helps to smooth and soften the skin, and may also reduce its roughness, cracking or irritation. Typical suitable emollients include mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural sonora jojoba oils, safflower oil, corn oil, liquid lanolin, cottonseed oil, grape seed oil, sweet almond oil, and peanut oil. Preferably, the emollient is a cocoglyceride, which is a mixture of mono, di- and triglycerides of cocoa oil, sold under the trade name of Myritol 331 from Henkel KGaA, or Dicaprylyl Ether available under the trade name Cetiol OE from Henkel KGaA or a $C_{12}$-$C_{15}$ Alkyl Benzoate sold under the trade name Finsolv TN from Finetex. One or more emollients may be present ranging in amounts from about 1 percent to about 10 percent by weight, preferably about 5 percent by weight. Another suitable emollient is DC 200 Fluid 350, a silicone fluid, available Dow Corning Corp.

Other suitable emollients include squalane, castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more emollients can optionally be included in the formulation.

A humectant is a moistening agent that promotes retention of water due to its hygroscopic properties. Suitable humectants include glycerin, polymeric glycols such as polyethylene glycol and polypropylene glycol, mannitol and sorbitol. Preferably, the humectant is Sorbitol, 70% USP or polyethylene glycol 400, NF. One or more humectants can optionally be included in the formulation in amounts from about 1 percent to about 10 percent by weight, preferably about 5 percent by weight. A dry-feel modifier is an agent which when added to an emulsion, imparts a "dry feel" to the skin when the emulsion dries. Dry feel modifiers can include talc, kaolin, chalk, zinc oxide, silicone fluids, inorganic salts such as barium sulfate, surface treated silica, precipitated silica, fumed silica such as an Aerosil available from Degussa Inc. of New York, N.Y. U.S.A. Another dry feel modifier is an epichlorohydrin cross-linked glyceryl starch of the type that is disclosed in U.S. Pat. No. 6,488,916.

It may be advantageous to incorporate additional thickening agents, such as, for instance, various Carbopols available from Noveon Co. Particularly preferred are those agents which would not disrupt the lamellar structure in the formulation of the final product, such as non-ionic thickening agents. The selection of additional thickening agents is well within the skill of one in the art.

Additional natural or synthetic substances can also be added to the compositions of the invention to protect from or delay its deterioration due to the action of oxygen in the air (oxidation). They may also reduce oxidation reactions in skin tissue. Such substances prevent oxidative deterioration which may lead to the generation of rancidity and nonenyzymatic browning reaction products. Typical suitable substances include propyl, octyl and dodecyl esters of gallic acid, butylated hydroxyanisole (BHA, usually purchased as a mixture of ortho and meta isomers), butylated hydroxytoluene (BHT), green tea extract, uric acid, cysteine, pyruvate, nordihydroguaiaretic acid, Vitamin A, Vitamin E and Vitamin C and their derivatives. One or more such substances can optionally be included in the composition in an amount ranging from about 0.001 to about 5 weight percent, preferably about 0.01 to about 0.5 percent.

Chelating agents are substances used to chelate or bind metallic ions, such as with a heterocylic ring structure so that the ion is held by chemical bonds from each of the participating rings. Suitable chelating agents include ethylene diaminetetraacetic acid (EDTA), EDTA disodium, calcium disodium edetate, EDTA trisodium, albumin, transferrin, desferoxamine, desferal, desferoxamine mesylate, EDTA tetrasodium and EDTA dipotassium, or combinations of any of these.

Fragrances are aromatic substances which can impart an aesthetically pleasing aroma to the sunscreen composition. Typical fragrances include aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. One or more fragrances can optionally be included in the sunscreen composition in an amount ranging from about 0.001 to about 5 weight percent, preferably about 0.01 to about 0.5 percent by weight.

Additional preservatives may also be used if desired and include well known preservative compositions such as benzyl alcohol, phenyl ethyl alcohol and benzoic acid, diazolydinyl, urea, chlorphenesin, iodopropynyl and butyl carbamate, among others.

The compositions of the invention can further comprise skin protectant active agents. Suitable examples include (with preferred weight percent ranges), Allantoin (0.5 to 2 percent); Aluminum hydroxide gel (0.15 to 5 percent); Calamine (1 to 25 percent); Cocoa butter (greater than 50); Cod liver oil (5 to 14 percent); Colloidal oatmeal; Dimethicone (1 to 30 percent); Glycerin (20 to 45 percent); Hard fat (greater than 50); Kaolin (4 to 20 percent); Lanolin (12.5 to 50 percent); Mineral oil (greater than 50 percent); Petrolatum (greater than 30 percent); Sodium bicarbonate; Topical starch (10 to 98 percent); White petrolatum (greater than 30 percent); Zinc acetate (0.1 to 2 percent); Zinc carbonate (0.2 to 2 percent); and Zinc oxide (1 to 25 percent).

The compositions of the invention may further include insect repelling components. The most widely used insect repelling active agent for personal care products is N,N-Diethyl-m-toluamide, frequently called "DEET" and available in the form of a concentrate containing at least about 95 percent DEET. Other synthetic chemical repellents include ethyl butylacetylaminoproprionate (also known as IR 3535), dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

Topical application of the compositions of the invention described herein to the hair or skin of a human will provide enhanced protection against deleterious effects of ultraviolet radiation (UVR). Thus, the subject invention further provides a method for protecting human skin and/or hair against the deleterious effects of solar radiation, more particularly UVR, which method comprises topically applying thereto an effective amount of the compositions as described herein. An esthetically beneficial result of exposure of skin to UVR (i.e., light radition wavelengths of from 280 nm to 400 nm) is the promotion of tanning of the human epidermis. Another benefit of sun exposure comes from production of vitamin D within the skin. UVR is typically divided into UV-A (light wavelengths from 320 to 400 nm) and UV-B (wavelengths ranging from 280 to 320 nm) regions. Overexposure to UV-B irradiation is generally understood to lead to skin burns and erythema. In addition, overexposure to UV-A radiation may cause a loss of elasticity of the skin and the appearance of wrinkles, promoting premature skin aging. Such irradiation promotes triggering of the erythemal reaction or amplifies this reaction in certain individuals and may even be the source of phototoxic or photoallergic reactions. It is increasingly believed that overexposure to UV-A may also lead to melanoma. Thus, the application of the compositions of the invention to the skin and/or hair of an individual will provide enhanced UVR photoprotection (UV-A and/or UV-B) of the skin and/or hair of the individual.

The sunscreen containing compositions of the invention are intended to provide a sun protection factor (SPF) rating of at least 2, with additional preferable embodiments having a sun protection factor of at least 5, in another embodiment at least 10, in another embodiment at least 15, in another embodiment at least 20, in another embodiment at least 25, in another embodiment at least 30, in another embodiment at least 35, in another embodiment at least 40, in another embodiment at least 45, in another embodiment at least 50, in another embodiment at least 55, in another embodiment at least 60, in another embodiment at least 65, in another embodiment at least 70, in another embodiment at least 75, in another embodiment at least 80, in another embodiment at least 85, in another embodiment at least 90, in another embodiment at least 95, and in another embodiment at least 100. The sunscreen containing compositions of the invention are also intended to provide U.S. FDA UV-A "star ratings" of at least one star, at least two stars, at least three stars and up to four stars. As demonstrated herein, by neutralizing the acid groups of the film forming polymer, a boost in SPF can be obtained while maintaining the amount of sunscreen active agent load in the composition. Thus, in an example embodiment of the invention, for two compositions containing equal amounts of sunscreen active agents, the SPF for the composition containing the partially or fully neutralized film forming agent may be greater than 125 percent of the composition containing un-neutralized film forming agents. In alternative example embodiments, the SPF for the composition containing the partially or fully neutralized film forming agent may be greater than 150 percent of the un-neutralized formulation, greater than 200 percent of the un-neutralized formulation, or greater than 300 percent of the un-neutralized formulation. Alternatively stated, an SPF greater than 125 percent of un-neutralized SPF is equivalent to saying the SPF for a composition containing the partially or fully neutralized polymer is greater than 1.25 times that which would be achieved using an un-neutralized formulation.

The invention will be further described by means of the following examples, which are not intended to limit the invention, as defined by the appended claims, in any manner.

Example 1—Sunscreen Composition

A sunscreen composition was prepared containing amine neutralizing agents and film forming polymer as follows. To a 250 ml beaker was added 3.0 g Avobenzone, 5.0 g Octisalate, 6.0 g Oxybenzone, 15.0 g Homosalate, and 1.0 g of Glycerine to a stirred solution containing 0.51 g of Dimethylstearylamine and 3.0 g of Dermacryl 79 (an acrylate copolymer containing 14% acrylic acid, available from National Starch and Chemical Co. Bridgewater, New Jersey) in 66.49 g of Ethanol. The composition was stirred until all components are dissolved. Similar compositions can be heated slightly to aid in dissolution.

Example 2—Evaluation of Effect of Neutralization on SPF of Sunscreen Formulations Sunscreen compositions were prepared as described above with varying levels and types of amine neutralizing agents. All compositions in this example contained Avobenzone (3.0 g), Octyl Salicylate (5.0 g), Oxybenzone (6.0 g), Homosalate (15.0 g), glycerin (1.0 g) and Dermacryl 79 (3.0 g) plus ethanol to bring the weight to 100 g.

All SPF measurements were conducted using poly(methyl methacrylate) (PMMA) plates (Schonberg GMBH & Co KG., 22457 Hamburg-Schnelsen, Germany) as the substrate to which the sunscreen formulas were applied. Test formulations were applied to the substrates at 1 mg/cm$^2$ and allowed to dry for 20 minutes. A PMMA plate treated with glycerin at 1 mg/cm$^2$ served as a reference and blank. The in vitro SPF of each formula was determined using an Optometrics SPF 290S Analzyer (Optometrics LLC, Ayer, MA; USA) equipped with a computer-controlled X-Y sampling stage and operated according to the manufacturer's instructions. A total of 12 in vitro SPF values were obtained for each formula using a different, non-overlapping position on each mounted substrate. All the SPF values reported are the average of 12 values measured for each formulation.

The results are shown in Table 2.

TABLE 2

SPF as a function of neutralization.

| Sample | 25% EtOH/ KOH (grams) | Triethanol amine (grams) | Dimethyl Stearyl amine (grams) | Percent neutralization of carboxylic acid groups | SPF in-vitro |
| --- | --- | --- | --- | --- | --- |
| 1 | 0 | 0 | 0 | 0 | 31 |
| 2 | 0.38 | | | 10 | 27 |
| 3 | 0.95 | | | 25 | 33 |
| 4 | 1.90 | | | 50 | 28 |
| 5 | | 0.10 | | 10 | 37 |
| 6 | | 0.25 | | 25 | 14 |
| 7 | | 0.50 | | 50 | 21 |
| 8 | | | 0.20 | 10 | 51 |
| 9 | | | 0.51 | 25 | 56 |
| 10 | | | 1.01 | 50 | 141 |

The results in Table 2 show the significant improvement in measured in vitro SPF with as little as 10 percent neutralization of the film forming polymer (sample 8) and that even higher levels of protections are possible with higher neutralization (sample 9 and 10). Similar results are not found with other common neutralizing agents that do not possess the long chain groups.

Example 3—Various Amines Used for SPF Boost

Sunscreens were prepared as described in example 2 and neutralized with the indicated amine to neutralize 25 percent of the carboxylic acid groups on the Dermacryl 79. Test formulations were applied to the PMMA substrate at 2 mg/cm$^2$. The results are shown in Table 3

TABLE 3

| Sample # | Amine | SPF |
| --- | --- | --- |
| 11 | Propylamine | 45 |
| 12 | Butylamine | 53 |
| 13 | Hexylamine | 82 |
| 14 | Octylamine | 102 |
| 15 | Decylamine | 93 |
| 16 | Dodecylamine | 76 |
| 17 | Diethylamine | 63 |
| 18 | Dihexylamine | 81 |
| 19 | Triethylamine | 54 |
| 20 | Tributylamine | 25 |
| 21 | Dimethylaminopropylcocamide | 69 |
| 22 | Cocamine | 83 |
| 23 | Dimethylcocamine | 52 |
| 24 | Dimethylstearylamine | 65 |
| 25 | Soyamine | 64 |
| 26 | Dimethylsoyamine | 63 |
| 27 | Dimethylerucylamine | 83 |
| 28 | Dimethylbehenylamine | 62 |
| 29 | PEG-15 Cocamine | 56 |
| 30 | PEG-15 Soyamine | 63 |
| 31 | PEG-2 Behenylamine | 71 |
| 32 | Jeffamine M-1000 | 57 |
| 33 | Jeffamine M-2070 | 34 |
| 34 | Control no neutralizer | 39 |

Sample 34 represents the control with no neutralization. These experiments show that, although compositions containing certain of the amines do not demonstrate a substantial boost in SPF, compositions containing examples of a wide variety of amines provide a large boost in SPF over the control.

Example 4—In Vivo SPF and Very Water Resistant Assays

Three sunscreen formulations were prepared and tested for sunscreen efficacy in a human SPF assay and Very Water Resistant Assay (FDA Final Monograph Protocol 7.22). The three formulations are Samples 1, 9, and 10 from Table 2 above. All three formulations were Ethanol based compositions containing, 3% Avobenzone, 5% Octyl Salicylate, 6% Oxybenzone, 15% Homosalate, 1.0% glycerin, 3% Dermacryl 79 (all percentages by weight of final formulation). The three formulations differed with respect to the percent neutralization of carboxylic acid groups of the film forming agent. Sample 1 had 0% neutralization, Sample 9 had 25% neutralization and Sample 10 had 50% neutralization. The amine neutralizing agent used for Samples 9 and 10 was dimethylstearylamine, which was added in an amount to achieve the desired neutralization level.

The SPF testing on each sample was conducted (according to Protocol 7.22) by first measuring the pre-immersion (static) average SPF, carrying out the immersion procedure, and then a second measurement post immersion to calculate very water resistant average SPF. Five subjects were tested for each sample. Results are shown in Table 4.

TABLE 4

| Sample | Avg SPF pre-immersion | Avg SPF post-immersion |
| --- | --- | --- |
| 1 | 31.8 | 29.2 |
| 9 | 56.5 | 55.8 |
| 10 | 78.3 | 78.3* |

*N = 4 for Sample 10 post-immersion. One of the five subjects exhibited erythema in all sub-sites to which the test composition was applied after water immersion. According to standard procedures, this subject was not used to calculate the average SPF value post immersion for Sample 10.

The data in Table 4 prove that the compositions of the invention provide a substantially increased in vivo SPF based on the presence of the amine-neutralized film forming agent and the formulations withstood Very Water Resistant Assay testing. Sample 9 (comprising 25% neutralization) showed an SPF of 178% (pre-immersion) and 191% (post-immersion) of the SPF of Sample 1. Sample 10 (comprising 50% neutralization) showed an SPF of 246% (pre-immersion) and an SPF of 268% (post immersion) of the SPF of Sample 1. The data demonstrate the compositions of the invention are very water resistant sunscreen compositions based on the negligible differences between the pre- and post-immersion SPF values.

Although certain presently preferred embodiments of the invention have been described herein, it will be apparent to those skilled in the art to which the invention pertains that variations and modifications of the described embodiments may be made without departing from the spirit and scope of the invention.

What is claimed:

1. A method for increasing the SPF of a composition that comprises at least one sunscreen active agent, less than about 5% by weight of water and, in a concentration greater than 1% by weight of the final composition, acrylates/octylacrylamide copolymer comprising a plurality of carboxylic acid groups, wherein the method comprises neutralizing at least 25% and up to 80% of the plurality of carboxylic acid groups exclusively with an amine-based neutralizing agent which is selected from alkyl amines; alkenyl amines; dialkyl amines; dialkenyl amines; dimethyl alkyl amines, wherein alkyl is stearyl or cocoyl; methyl dialkyl amines, wherein alkyl is stearyl or hexadecyl; and dimethyl alkenyl amines, wherein alkenyl is oleic, linoleic or linolenic, the acrylates/octylacrylamide copolymer being the only polymer present in the composition.

2. The method of claim 1, wherein the amine-based neutralizing agent comprises dimethyl stearyl amine.

3. The method of claim 1, wherein the acrylates/octylacrylamide copolymer is present in a concentration of up to 10% by weight of the final composition.

4. The method of claim 1, wherein the acrylates/octylacrylamide copolymer is present in a concentration of up to 5% by weight of the final composition.

5. The method of claim 1, wherein up to 70% of the plurality of acid groups are neutralized by the amine-based neutralizing agent.

6. The method of claim 1, wherein at least 50% of the plurality of acid groups are neutralized by the amine-based neutralizing agent.

7. The method of claim 1, wherein neutralizing the carboxylic acid groups of the acrylates/octylacrylamide copolymer with the amine-based neutralizing agent results in an SPF rating which is greater than 1.5 times the SPF rating of the composition without neutralized carboxylic acid groups.

8. The method of claim 1, wherein neutralizing the carboxylic acid groups of the acrylates/octylacrylamide copolymer with the amine-based neutralizing agent results in an SPF rating which is greater than 2 times the SPF rating of the composition without neutralized carboxylic acid groups.

9. The method of claim 1, wherein the composition exhibits a sun protection factor (SPF) of at least 50.

10. The method of claim 1, wherein the composition comprises less than about 1% by weight of water.

11. The method of claim 1, wherein the composition is sprayable.

12. A method for increasing the SPF of a composition that comprises at least one sunscreen active agent, less than about 1% by weight of water and, in a concentration greater than 1% by weight of the final composition, acrylates/octylacrylamide copolymer comprising a plurality of carboxylic acid groups, wherein the method comprises neutralizing at least 40% and up to 70% of the plurality of carboxylic acid groups exclusively with an amine-based neutralizing agent which is selected from dimethyl alkyl amines wherein alkyl is stearyl or hexadecyl, the acrylates/octylacrylamide copolymer being the only polymer present in the composition.

13. The method of claim 12, wherein the amine-based neutralizing agent is dimethyl stearyl amine.

14. The method of claim 12, wherein the acrylates/octylacrylamide copolymer is present in a concentration of up to 5% by weight of the final composition.

15. The method of claim 12, wherein neutralizing the carboxylic acid groups of the acrylates/octylacrylamide copolymer with the amine-based neutralizing agent results in an SPF rating which is greater than 1.5 times the SPF rating of the composition without neutralized carboxylic acid groups.

16. The method of claim 12, wherein the composition is sprayable.

17. A method for increasing the SPF of a sprayable composition that comprises at least one sunscreen active agent, less than about 1% by weight of water and, in a concentration greater than 1% and up to 5% by weight of the final composition, acrylates/octylacrylamide copolymer comprising a plurality of carboxylic acid groups, wherein the method comprises neutralizing at least 25% and up to 80% of the plurality of carboxylic acid groups with dimethyl stearyl amine, which results in an SPF rating that is greater than 1.5 times the SPF rating of the composition without neutralized carboxylic acid groups, the acrylates/octylacrylamide copolymer being the only polymer present in the composition.

* * * * *